United States Patent [19]

Kapitanov et al.

[11] 4,355,751
[45] Oct. 26, 1982

[54] SURGICAL INSTRUMENT FOR SUTURING CUTANEOUS TISSUE

[76] Inventors: Nikolai N. Kapitanov, ulitsa Iriny Levchenko, 3, kv. 9; Natalya P. Petrova, 1 Novokuzminskaya ulitsa, 4, kv. 40; Vsevolod V. Judenich, Leninsky prospekt, 87, kv. 370; Vladimir P. Kharchenko, ulitsa Lesevskaya, 1, korpus 4, kv. 761; Boris A. Smirnov, ulitsa Borisa Galushkina, 17, kv. 26; Vladimir V. Ippolitov, ulitsa Lavochkina, 6, korpus 2, kv. 143; Nadezhda M. Lankina, Shenkursky proezd, 12, kv. 123, all of, Moscow, U.S.S.R.

[21] Appl. No.: 100,543

[22] Filed: Dec. 5, 1979

[30] Foreign Application Priority Data

Dec. 8, 1978 [SU] U.S.S.R. ............... 2719347

[51] Int. Cl.³ .................. B25C 5/02; A61B 17/32
[52] U.S. Cl. .................. 227/19; 227/DIG. 1; 227/155
[58] Field of Search ............ 227/DIG. 1, 19, 155; 128/334 R

[56] References Cited

U.S. PATENT DOCUMENTS

| 3,822,818 | 7/1974 | Strekopytov et al. ... 227/DIG. 1 X |
| 3,858,783 | 1/1975 | Kapitonov et al. ...... 227/DIG. 1 X |
| 3,889,683 | 6/1975 | Kapitanov et al. ...... 227/DIG. 1 X |

*Primary Examiner*—Paul A. Bell
*Attorney, Agent, or Firm*—Steinberg & Raskin

[57] ABSTRACT

Described herein is a surgical instrument for suturing cutaneous tissue, especially scar tissue, when stitching on skin grafts, said instrument comprising a supporting body and a staple body which are hinged to each other so as to be capable of being brought together or apart. A staple magazine is provided on the staple body of the instrument, and an ejector is provided for driving the staples from the staple body into the stitching unit. The stitching unit incorporates a single needle-shaped die with an L-shaped needle, said needle being mounted on the supporting body, and a slot formed at the end of the staple body through which the die needle passes when suturing. The needle-shaped die has two recesses, one of which communicates with the magazine through the groove provided in the supporting body, while the other of which, upon bringing the instrument bodies together, is located against a special groove in the staple body, communicating with the staple magazine and with the base of the slot.

2 Claims, 5 Drawing Figures

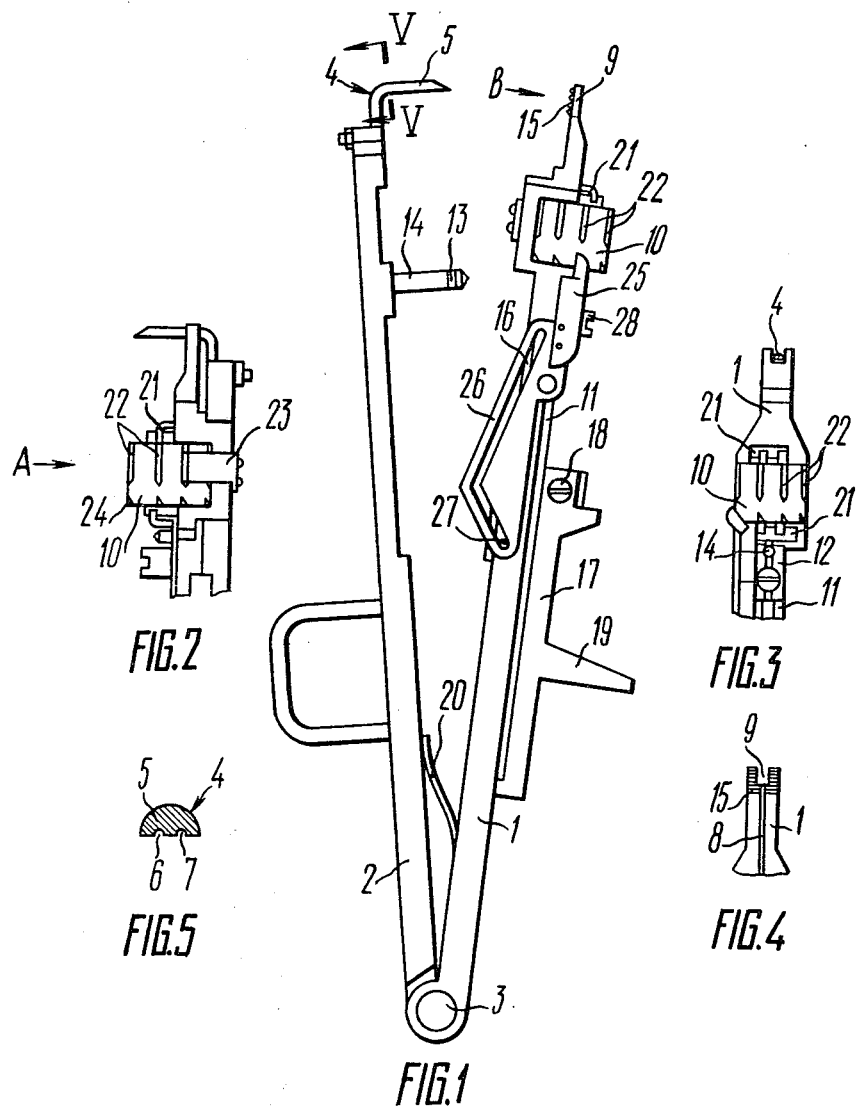

SURGICAL INSTRUMENT FOR SUTURING CUTANEOUS TISSUE

The present invention relates to surgical instruments and more specifically to surgical instruments for suturing cutaneous tissue. The invention is most advantageously applicable for instruments adapted to stitch up skin graft to cutaneous tissue affected by burns.

One prior-art surgical instrument for suturing soft tissues, in particular, cutaneous tissue and which utilizes U-shaped metallic staples (cf. e.g. USSR Inventor's Certificate No. 240,171 dated Feb. 19, 1964) is known to comprise a staple body and a supporting body hingedly-joined together and adapted to be moved apart by virtue of a flat spring. The suturing staples are enclosed in a multiple-load magazine, wherefrom they are advanced to the stitching unit, which is located at the instrument end and is established by two needles or needle-shaped dies, each having a recess communicating through the grooves on the needle surface, with the grooves in the bulk of the bodies. The grooves communicate with the staple magazine through longitudinal slots running lengthwise in each of the bodies, said magazine being locked in place on the staple body by a pin and a spring. The magazine has a longitudinal slot for the staple ejector and a number of transverse bevelled staple grooves spaced somewhat apart. The side walls of the magazine have a number of holes for locking the magazine in place by the pins provided on the staple and supporting members, whereas the end faces of the magazine have slots and holes for fixing the spring that forces the magazine against the stable body, thus keeping it from falling out when the bodies are moved apart. The staple ejector is situated on the staple body and has a knurled projection at one of its ends, adapted for the ring to thrust against and travel. The pin located on the staple body behind the knurled projection is to restrict the ejector return travel when being retracted to its extreme position after the suturing has been performed. The middle portion of the supporting body has a number of side slits adapted to have a lock pass therethrough, said lock being located on the knurled ejector projection and serving for locking both of the bodies when the ejector is being advanced. The height of staple bending is adjusted by a special restrictor.

The above-discussed instrument operates as follows. The magazine is loaded with staples, whereupon it is fitted into the slot of the staple body in such a manner that the pin on the staple body should catch the bottommost hole of the magazine. Then the magazine is locked from above by a spring to prevent the same from falling out of the instrument. Next the margins of the skin tissue being sutured are placed on the needles, the staple and supporting bodies are brought together and locked by advancing the ejector beyond the knurled projection. As a result, the ejector brings a staple from the magazine slots and inserts it first into the grooves of the staple and supporting bodies and then into the grooves of the needles, so that the staple legs become bent. This done, the ejector is returned into its rearmost position, the flat spring arranged in between the staple and supporting bodies moving them apart, and the instrument removed from the sutured tissue. Thereupon the magazine is forced out of the staple body and advanced to the next hole which is caught by the pin. Thus, the instrument is ready for stitching the tissue with a next staple.

Once the staples of the magazine has been used up, the empty magazine can be replaced by a loaded one, and the suturing can be continued.

The above-discussed known instrument, however, is capable of suturing soft tissues only. When suturing scorched tissue which is characterized by a considerable change in its structure, the needles fail to prick through the skin on account of its abnormally increased density so that when the tissue is then compressed by the instrument the needles turn the tissue so that the latter becomes situated between the needles instead of being positioned thereagainst. For this reason the staple fails to puncture the tissue during the suturing and is bent idle, i.e., no suture is established.

It is an essential object of the present invention to provide such a stitching unit of a surgical instrument for suturing cutaneous tissue that would render possible the suturing of scar tissue having an increased density, and the formation of a reliable suture.

This and other objects are accomplished due to the fact that in a surgical instrument for suturing cutaneous tissue using U-shaped staples, comprising a supporting body, a stitching unit, guide grooves for advancing the U-shaped staples from a change magazine of the staple body to the stitching unit for subsequently passing said staples through the tissue being sutured and bending them, as well as an ejector located on the staple body and adapted for driving the staples out from the change or replaceable magazine into the guides, according to the invention, the stitching unit has a single L-shaped needle fixed on the supporting body, and a slot provided at the end of the staple body and adapted for the needle-shaped die to pass, while the staple body has a longitudinal groove communicating with the base of the slot and with the magazine, and the needle-shaped die has two recesses, of which one recess communicates with the groove in the supporting body which becomes communicated with the magazine during suturing, and the other recess is so arranged that it gets communicated with the groove in the staple body upon passing the needle into the slot.

An advantageous feature of the proposed device resides in that when suturing scorched scar tissue the needle of the stitching unit which is located on the supporing body, pricks the tissue being sutured, and upon bringing the staple and supporting bodies together the slot of the staple body facilitates the feeding of the resilient scar tissue towards the needle for further advancing said tissue to the zone of stitching.

It is expedient that a knurled area be provided at the end of the staple body within the zone of the slot so as to ensure more reliable gripping of the tissue being sutured.

In what follows the present invention is illustrated in a detailed description of a specific exemplary embodiment thereof with reference to the attached drawings, wherein:

FIG. 1 is a general view of the instrument when unlocked, according to the invention;

FIG. 2 is a fragmentary side-elevation view of the instrument when locked, according to the invention;

FIG. 3 is a fragmentary view of the instrument, taken along the arrow A in FIG. 2, according to the invention;

FIG. 4 is a fragmentary view of the instrument, taken along the arrow B in FIG. 1; and FIG. 5 is a fragmentary sectional view of the instrument, taken along the line V—V in FIG. 1.

The instrument for suturing skin grafts to scorched tissue comprises a staple body 1 (FIG. 1) and a supporting body 2, both being interconnected through a hinge joint 3. A needle-shaped die 4 is fixed at the free end of the supporting body 2, said die having an L-shaped needle 5. Recesses 6 and 7 (FIG. 5) are formed in the inner surface of the needle 5 at the bend thereof, said recesses being arranged parallel to each other. Recess 6 communicates through the groove (not shown) in the needle 5 of the needle-shaped die 4, with a groove (not shown) in the supporting body, and said groove is communicated with a staple magazine 10 when the bodies 1 and 2 are locked together. The end of a groove 8 (FIG. 4) in the staple body 1 is at the same level with the base of a slot 9 provided at the end of the staple body which is adapted to receive needle 5 of the die 4 which passes therethrough. The recess 7 is so arranged that when the bodies 1 and 2 are locked together, said recess is situated against the groove 8 at some clearance therewith. The groove 8 of the staple body communicates at its opposite end with the staple magazine 10 through its opposite end.

The bodies 1 and 2 are held locked together by a lock 11 having a yoke 12 adapted to interact with slots 13 of a pin 14 (FIG. 1).

A knurling 15 (FIGS. 1 and 4) is provided on the end portion of the staple body within the zone where the slot 9 is situated, for reliably gripping the tissue being sutured and preventing slippage thereof. An ejector 16 is linked to a carriage 17 through a screw 18. The carriage 17 has a lug 19 serving as a rest for the surgeon's finger during suturing. A spring 20 is provided to normally urge the bodies 1 and 2 apart from each other, said spring being fixed to the staple body 1. Each of the magazines 10 has eight holes through which the ejector 16 can pass in order to advance the staples. The magazine 10 is locked into one of eight possible positions by swivel locks 21.

Grooves 22 are provided on the outside surface of the magazine 10 for a retainer 23, as well as stops 24 for interacting with the ends of a retainer spring 25 fixed to the end of a lever 26 pivotally mounted on the staple body.

The ejector 16 has a pin 27 fixed thereto which passes through an angled slot 32 formed in the lever 26.

A screw 28 is provided for adjusting the suturing gap.

The herein-proposed instrument for suturing cutaneous tissue operates as follows:

Using the screw 28 a required suturing gap is established, i.e., the distance between the ejector end and the needle-shaped die 4 is set.

The magazine 10, loaded with staples, is fitted into the socket of the staple body 1 and locked in place by the locks 21 which permit the magazine to rotate or swivel as described below. With the bodies 1 and 2 set apart the instrument is brought to the tissues being sutured with the needle-shaped die facing said tissues, whereupon some tissue is caught by the end of the staple body 1 and urged against the needle-shaped die 4. In this case the knurling 15 of the staple body 1 facilitates the gripping of a certain amount of tissue and reliably holds it against slippage. When the tissue is compressed the needle-shaped die remains stationary, while the end of the staple body feeds the tissue onto said die. The needle passes through slot 9 as a result of further compression of the staple body 1 and feeds the tissue along the needle into the suturing zone. Upon moving the lug 19 of the carriage 17 towards needle 5 the pin 27 fixed to the ejector 16 and which passes through slot 32 of lever 26 pivots the lever 26 which, acts through the spring as fixed thereto and which rests against the stops 24, to cause the magazine 10 to rotate into an indexed position. Such rotation occurs as the ejector pin 27 moves over the length of the short rectilinear portion of the angle slot 32. The magazine 10 is then fixed against further rotation by the retainer 23 which rests against a respective groove 22. At the same time the yoke 12 of the lock 11 engages the slot 13 of the pin 14, whereby the lock 11 locks the bodies 1 and 2 in the operating position. The carriage 17 is then further advanced to advance ejector 16 into the aligned opening of magazine 10 to engage the staple therein and urge it in a forward direction. Further advancement of the ejector 16 results in the staple (not shown) being pushed out of the magazine 10 whereupon it is fed towards the needle-shaped die with its legs sliding over groove 8 of the staple body and the cooperating groove (not shown) 8a in the supporting body.

Eventually, a first one of the staple legs engages the groove in the needle, while the other leg continues to slide along the groove 8 of the staple body 1. Upon leaving the staple body 1 the other leg enters the recess 7 of the needle-shaped die 4, whereas the first staple leg slides along the groove of the needle-shaped die and enters into the recess 6. Further advancement of the staple by the ejector 16 towards the recesses 6 and 7 of the needle-shaped die results in bending of the staple. Thus, in this manner part of the tissue is sutured by the staple.

Thereupon the carriage 17 is retracted by moving lug 19 and the ejector 16 is returned to the initial position. During the retracting movement of the carriage 17, the pin 27 rotates the lever 26 and the spring 25 fixed thereto to its initial position. In this manner, the spring 25 engages another stop 24.

Next the spring 20 urges the bodies 1 and 2 apart, whereupon the needle-shaped die 4 is withdrawn from the sutured tissue.

To suture the tissue with a next staple the entire cycle of operations is repeated until the supply of the staples in the magazine is exhausted.

Thus, an eight-staple suture can be applied with the use of a loaded staple magazine.

Having replaced the empty magazine with a loaded one the suture application procedure can be continued.

Through a preferred embodiment of the instrument for staple suturing of cutaneous tissue has been disclosed in the foregoing description, it should be understood that it is by no means limitative on the scope of claims presented by the applicants, which is defined only by the claims appended hereto, and that some changes may occur to those skilled in the art.

What we claim is:

1. A surgical instrument for suturing cutaneous tissue using U-shaped staples, comprising a supporting body and a staple body, said bodies being pivotally connected so as to be movable together during suturing and movable apart after suturing, a replaceable magazine provided on the staple body and adapted to accommodate said U-shaped staples, a stitching unit to which said staples are fed from the magazine, said unit being adapted to pass the staples through the tissues being sutured and bend said staples to establish a suture, said stitching unit including a single needle-shaped die having an L-shaped needle fixed to the supporting body, and a slot provided at the end of the staple body which is positioned so as to be receivable of the needle of said needle-shaped die when said supporting and staple bodies are move together so that the needle of said needle-shaped die passes therethrough, said staple body having a longitudinal groove formed therein which communicates through one of its ends with the base of said slot in the stitching unit, and which communicates through its other end with a staple receiving opening formed in the magazine, a groove provided in the supporting body arranged such that, when said bodies are moved together, said groove communicates with said staple receiving opening formed in the magazine, said needle-shaped die having two recesses, one of said recesses communicating with said groove formed in the supporting body, while the other recess is arranged such that when the needle of said needle-shaped die enters said slot, said recess enters into communication with the groove formed in the staple body, and an ejector for driving the staples out of the magazine.

2. A surgical instrument as claimed in claim 1, wherein knurling is provided on the staple body within the zone of said slot.

* * * * *